US012370367B2

United States Patent
Ince et al.

(10) Patent No.: US 12,370,367 B2
(45) Date of Patent: Jul. 29, 2025

(54) SYSTEM AND METHOD FOR DETERMINING DEEP BRAIN STIMULATION PARAMETERS

(71) Applicant: University of Houston System, Houston, TX (US)

(72) Inventors: Nuri F. Ince, Humble, TX (US); Musa Ozturk, Houston, TX (US); Ashwin Viswanathan, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 229 days.

(21) Appl. No.: 17/400,312

(22) Filed: Aug. 12, 2021

(65) Prior Publication Data
US 2022/0047873 A1 Feb. 17, 2022

Related U.S. Application Data

(60) Provisional application No. 63/068,155, filed on Aug. 20, 2020, provisional application No. 63/066,141, filed on Aug. 14, 2020.

(51) Int. Cl.
*A61N 1/36* (2006.01)
*A61N 1/05* (2006.01)

(52) U.S. Cl.
CPC ....... *A61N 1/36171* (2013.01); *A61N 1/0534* (2013.01); *A61N 1/36067* (2013.01)

(58) Field of Classification Search
CPC .............. A61N 1/36171; A61N 1/0534; A61N 1/36067; A61N 1/36139; A61N 1/36185;
(Continued)

(56) References Cited

U.S. PATENT DOCUMENTS

| 6,480,743 B1 | 11/2002 | Kirkpatrick et al. |
| 8,600,513 B2 | 12/2013 | Aur et al. |

(Continued)

FOREIGN PATENT DOCUMENTS

| EP | 1940508 B1 | 12/2011 |
| JP | 2012504458 A | 2/2012 |

(Continued)

OTHER PUBLICATIONS

International Preliminary Report on Patentability dated May 17, 2022 issued in corresponding PCT Appln. No. PCT/US2021/045921.

(Continued)

*Primary Examiner* — Benjamin J Klein
*Assistant Examiner* — Daniel Tehrani
(74) *Attorney, Agent, or Firm* — George Likourezos; Carter, DeLuca & Farrell LLP

(57) ABSTRACT

A method of determining brain stimulation parameters includes applying Low Frequency Stimulation (LFS) to a contact of a multi-contact electrode implanted in a target structure in an individual's brain. Evoked Compound Activity (ECA) evoked in the target structure by the LFS is measured. A range of frequencies for delivering brain stimulation within a predetermined range based on a phase space extracted from the ECA is determined. Stimulation frequencies are applied to the contact of the multi-contact electrode within the determined range of frequencies. High Frequency Oscillations (HFO) evoked in the target structure by the applied stimulation frequencies within the determined range are measured. A frequency evoking HFO above a predetermined threshold is determined. The determined frequency is selected as a treatment frequency for the target structure.

20 Claims, 11 Drawing Sheets

(58) Field of Classification Search
CPC .............. A61N 1/36135; A61N 1/0529; A61N 1/0531; A61B 5/293; A61B 5/377; A61B 5/4064; A61B 5/4082; A61B 5/369; A61B 5/374; A61B 5/4094
See application file for complete search history.

(56) References Cited

U.S. PATENT DOCUMENTS

| | | | |
|---|---|---|---|
| 8,849,392 | B2 | 9/2014 | Lozano |
| 8,914,119 | B2 | 12/2014 | Wu et al. |
| 9,604,056 | B2 | 3/2017 | Starr et al. |
| 10,463,860 | B2 | 11/2019 | Sinclair et al. |
| 2007/0060974 | A1 | 3/2007 | Lozano |
| 2009/0099474 | A1* | 4/2009 | Pineda ............ A61B 5/386 600/545 |
| 2012/0271375 | A1* | 10/2012 | Wu ............ A61N 1/36153 607/45 |
| 2014/0350634 | A1 | 11/2014 | Grill et al. |
| 2016/0030735 | A1* | 2/2016 | Ouchouche ........ A61N 1/3605 607/116 |
| 2016/0121124 | A1* | 5/2016 | Johanek ............ A61N 1/37247 607/62 |
| 2018/0110991 | A1 | 4/2018 | Molnar et al. |
| 2018/0185649 | A1* | 7/2018 | Michaeli ............ A61N 1/0534 |
| 2020/0086047 | A1 | 3/2020 | Lozano et al. |
| 2020/0138324 | A1* | 5/2020 | Sinclair ............ A61N 1/36139 |

FOREIGN PATENT DOCUMENTS

| | | |
|---|---|---|
| JP | 2020521544 A | 7/2020 |
| WO | 2018213872 A1 | 11/2018 |

OTHER PUBLICATIONS

Sinclair et al., "Deep Brain Stimulation for Parkinson's Disease Modulates High-Frequency Evoked and Spontaneous Neural Activity", Neurobiology of Disease, vol. 130, Nov. 26, 2019, retrieved on [Oct. 12, 2021] Retrieved from the Internet. <URL:https://WWW. ncbl.nlm.nih.gov/pmc/articles/PMC6879321/pdf/EMS84988.pdf> entire document.

Zumsteg et al. "Rhythmic Cortical EEG Synchronization With Low Frequency Stimulation of the Anterior and Medial Thalamus for Epilepsy", Clinical Neurophysiology, vol. 117, Issue 10, Oct. 2006, pp. 2272-2278, 21.08.2006, retrieved on [Dec. 10, 2021]. Retrieved from the internet https://d 1wqtxts 1 xzle 7 .cloudfront.neU526504 73/i.clinph.2006.06. 70720170417-31363-618fp2-wlJh-cover-page-v2.pdf?Expires=1634154686&Signature=UvAlcBHQ-MGthxTp1 rgwKf-C05gEM290EihVByYk8E4HJDpl.

Kent et al. "Measurement of Evoked Potentials During Thalamic Deep Brain Stimulation", NIH 1-20 Public Access. Brain Stimulation vol. 8, Jan. 1, 2016, retrieved on [Oct. 12, 2021]. Retrieved from the internet <URL:https://www.ncbi.nlm.nih.gov/pmc/articles/PMC4277712/pdf/nihms640436.pdf> entire document.

International Search Report and Written Opinion dated Dec. 1, 2021 issued in corresponding PCT Appln. No. PCT/US2021/045921.

Korean Office Action issued by the Korean Patent Office in connection with Korean Patent Application No. 10-2023-7008918, dated Jun. 20, 2023.

Canadian Examination Report issued by the Canada Intellectual Property Office in connection with International Application No. 3,189,309, dated Aug. 17, 2023.

Japanese Office Action issued by the Japanese Patent Office in connection with International Application No. JP 2023-510450, dated Aug. 22, 2023.

Examination Report issued by the Canadian Patent Office in connection with International Application No. 3,189,309, dated Feb. 6, 2024.

Extended European Search Report issued by the European Patent Office in connection with International Application No. 21856776.6, dated Aug. 13, 2024.

Musa Ozturk, "Pharmacological and Electroceutical Modulations of Local Field Potentials in Parkinson's Disease", University of Houston, pp. 1-166, May 2020.

Maurizio Zibetti, MD, et al., "Low-Frequency Stimulation of Globus Pallidus Internus for Axial Motor Symptoms of Parkinson's Disease", Movement Disorders, pp. 1-2, 2015.

A. Benabid, et al., "Deep brain stimulation of the subthalamic nucleus for the treatment of Parkinson's Disease", www.thelancet.com/neurology, vol. 8, pp. 1-16, Jan. 2009.

Fumin Jia, Ph.D., et al., "Deep Brain Stimulation at Variable Frequency to Improve Motor Outcomes in Parkinson's Disease", Movement Disorders, pp. 1-4, 2018.

Examination Report issued by the Canadian Patent Office in connection with International Application No. 3,189,309, dated May 31, 2024.

Musa Ozturk, et al., "Electroceutically induced subthalamic high frequency oscillations and evoked compound activity may explain the mechanism of therapeutic stimulation in Parkinson's Disease", Research Square, pp. 1-30, Oct. 8, 2020.

Japanese Office Action issued by the Japanese Patent Office in connection with International Application No. JP 2023-510450, dated May 21, 2024.

Japanese Office Action issued by the Japanese Patent Office in connection with International Application No. JP 2023-510450 dated, dated Nov. 26, 2024. (Translation).

* cited by examiner

SYSTEM AND METHOD FOR DETERMINING DEEP BRAIN STIMULATION PARAMETERS

CROSS-REFERENCE TO RELATED APPLICATION

This U.S. Non-Provisional patent application claims priority to U.S. Provisional Patent Application No. 63/066,141, filed on Aug. 14, 2020, and U.S. Provisional Patent Application No. 63/068,155, filed on Aug. 20, 2020.

GOVERNMENT SUPPORT

This invention was made with government support under 1343548 awarded by the National Science Foundation. The government has certain rights in the invention.

FIELD

The present disclosure relates to deep brain stimulation, more specifically, to systems and methods for determining deep brain stimulation parameters.

BACKGROUND

Current brain stimulators are programmed by trial and error. This can be extremely time consuming. For example, programing can take hours per sessions across multiple sessions, and follow up programming sessions may be needed. Therefore, there is a need for systems that can optimize the programming parameters based on the response of the brain in an automated and objective manner.

SUMMARY

Provided in accordance with aspects of the present disclosure is a method of locating an implantation site in the brain including inserting a plurality of multi-contact electrodes into a region of a target structure in an individual's brain. High Frequency Stimulation (HFS) is applied to a contact of a multi-contact electrode of the plurality of multi-contact electrodes. High Frequency Oscillations (HFO) induced in the region of the target structure by the HFS are measured. Evoked Compound Activity (ECA) evoked in the region of the target structure by the HFS is measured. It is determined if at least one of the HFO and the ECA is above a predetermined threshold. If at least one of the HFO and the ECA is above the predetermined threshold, a location of the contact of the multi-contact electrode is identified as a site for electrode implantation in the individual's brain.

In an aspect of the present disclosure, if the HFO and the ECA is below the predetermined threshold, a second high frequency stimulation is applied to a second contact of the multi-contact electrode of the plurality of multi-contact electrodes. If no site for electrode implantation in the individual's brain is identified, the plurality of multi-contact electrodes is moved to a second region in the individual's brain.

In an aspect of the present disclosure, at least one electrode is configured for Deep Brain Stimulation (DBS) to the site for electrode implantation in the individual's brain.

In an aspect of the present disclosure, the target structure is the Subthalamic Nucleus (STN).

In an aspect of the present disclosure, measuring HFO and ECA is performed intraoperatively.

In an aspect of the present disclosure, the HFS is greater than 100 Hz.

In an aspect of the present disclosure, the HFO includes an oscillation pattern greater than 300 Hz.

In an aspect of the present disclosure, the ECA includes a resonance pattern between 200-450 Hz.

In an aspect of the present disclosure, the plurality of multi-contact electrodes is inserted into a brain of an individual having Parkinson's Disease (PD).

Provided in accordance with aspects of the present disclosure is a system for locating a site for electrode implantation in the brain including a plurality of multi-contact electrodes. The plurality of multi-contact electrodes is configured for insertion into a region of a target structure in an individual's brain. A stimulating device is in electrical communication with each of the plurality of multi-contact electrodes. The stimulating device applies High Frequency Stimulation (HFS) to each of the plurality of multi-contact electrodes. The stimulating device is configured to selectively apply the HFS to subset of contacts of one multi-contact electrode of the plurality of multi-contact electrodes. A recording device is configured to measure High Frequency Oscillations (HFO) of Local Field Potentials induced in the region of the target structure by the HFS. The recording device is configured to measure Evoked Compound Activity (ECA) evoked in the region of the target structure by the HFS. A signal processing unit is in communication with the recording device. The signal processing unit determines if the at least one of the HFO and the ECA is above a predetermined threshold to identify a location of the one contact of the multi-contact electrode as a site for electrode implantation in the individual's brain.

In an aspect of the present disclosure, a visualization unit visually displays the measured HFO and ECA.

In an aspect of the present disclosure, a switching unit controls the HFS applied by the stimulating device. If the at least one of the HFO and ECA is below the predetermined threshold, the switching unit is configured to control the HFS to apply a second high frequency stimulation to a second contact of the multi-contact electrode of the plurality of multi-contact electrodes.

In an aspect of the present disclosure, the recording device is configured to measure HFO and ECA induced in Local Field Potentials intraoperatively.

Provided in accordance with aspects of the present disclosure is a method of determining brain stimulation parameters including applying Low Frequency Stimulation (LFS) to a subset of contacts of a multi-contact electrode implanted in a target structure in an individual's brain. Evoked Compound Activity (ECA) evoked in the target structure by the LFS is measured. A range of frequencies for delivering brain stimulation within a predetermined range based on a phase space extracted from the ECA is determined. Stimulation frequencies are applied to the contact of the multi-contact electrode within the determined range of frequencies. High Frequency Oscillations (HFO) evoked in the target structure by the applied stimulation frequencies within the determined range are measured. A frequency evoking HFO above a predetermined threshold is determined. The determined frequency is selected as a treatment frequency for the target structure.

In an aspect of the present disclosure, the target structure is the Subthalamic Nucleus (STN).

In an aspect of the present disclosure, measuring HFO and ECA is performed chronically.

In an aspect of the present disclosure, the HFS is greater than 100 Hz.

In an aspect of the present disclosure, the LFS is less than 100 Hz.

In an aspect of the present disclosure, the selected frequency is greater than 100 Hz.

In an aspect of the present disclosure, the selected frequency can be any frequency in the 100-200 Hz range.

In an aspect of the present disclosure, the measured HFO evoked in the target structure is between 200-450 Hz.

In an aspect of the present disclosure, the ECA includes a resonating response above a predetermined threshold.

In an aspect of the present disclosure, if the ECA is below a predetermined threshold, a second LFS is applied to a second subset of contacts of the multi-contact electrode in a different location within the target structure than the contact of the multi-contact electrode.

In an aspect of the present disclosure, the multi-contact electrode is configured for Deep Brain Stimulation (DBS) of the target structure.

In an aspect of the present disclosure, the target structure is the Subthalamic nucleus (STN).

In an aspect of the present disclosure, the individual has Parkinson's Disease (PD).

Provided in accordance with aspects of the present disclosure is a system for determining deep brain stimulation parameters including at least one multi-contact electrode configured for implanting in a target structure in an individuals' brain. A stimulating device is in electrical communication with the at least one multi-contact electrode. The stimulating device is configured to apply Low Frequency Stimulation (LFS) or High Frequency Stimulation (HFS) to the at least one multi-contact electrode. A recording device is configured to record at least one of Evoked Compound Activity (ECA) evoked in the target structure by the LFS and High Frequency Oscillations (HFO) evoked in the target structure by the HFS. A signal processing unit is in communication with the recording device. The signal processing unit determines a range of frequencies for delivering brain stimulation within a predetermined range based on a phase space extracted from the ECA. The signal processing unit analyzes High Frequency Oscillations (HFO) evoked in the target structure by the applied stimulation frequencies within the determined range. A parameter optimization unit determines a frequency evoking HFO above a predetermined threshold, and selects the frequency as a treatment frequency for the target structure.

In an aspect of the present disclosure, the stimulating device is configured to selectively apply the LFS or HFS to subset of contacts of one multi-contact electrode of the plurality of multi-contact electrodes.

In an aspect of the present disclosure, at least one of the stimulating device, the recording device, the signal processing unit, and the parameter optimization unit are implanted in the individual's chest.

In an aspect of the present disclosure, an input/output (I/O) unit is in electrical communication with the stimulating device, the recording device, the signal processing unit, and the parameter optimization unit.

BRIEF DESCRIPTION OF THE DRAWINGS

Various aspects and features of the present disclosure are described hereinbelow with reference to the drawings wherein.

DETAILED DESCRIPTION

Figure 1:
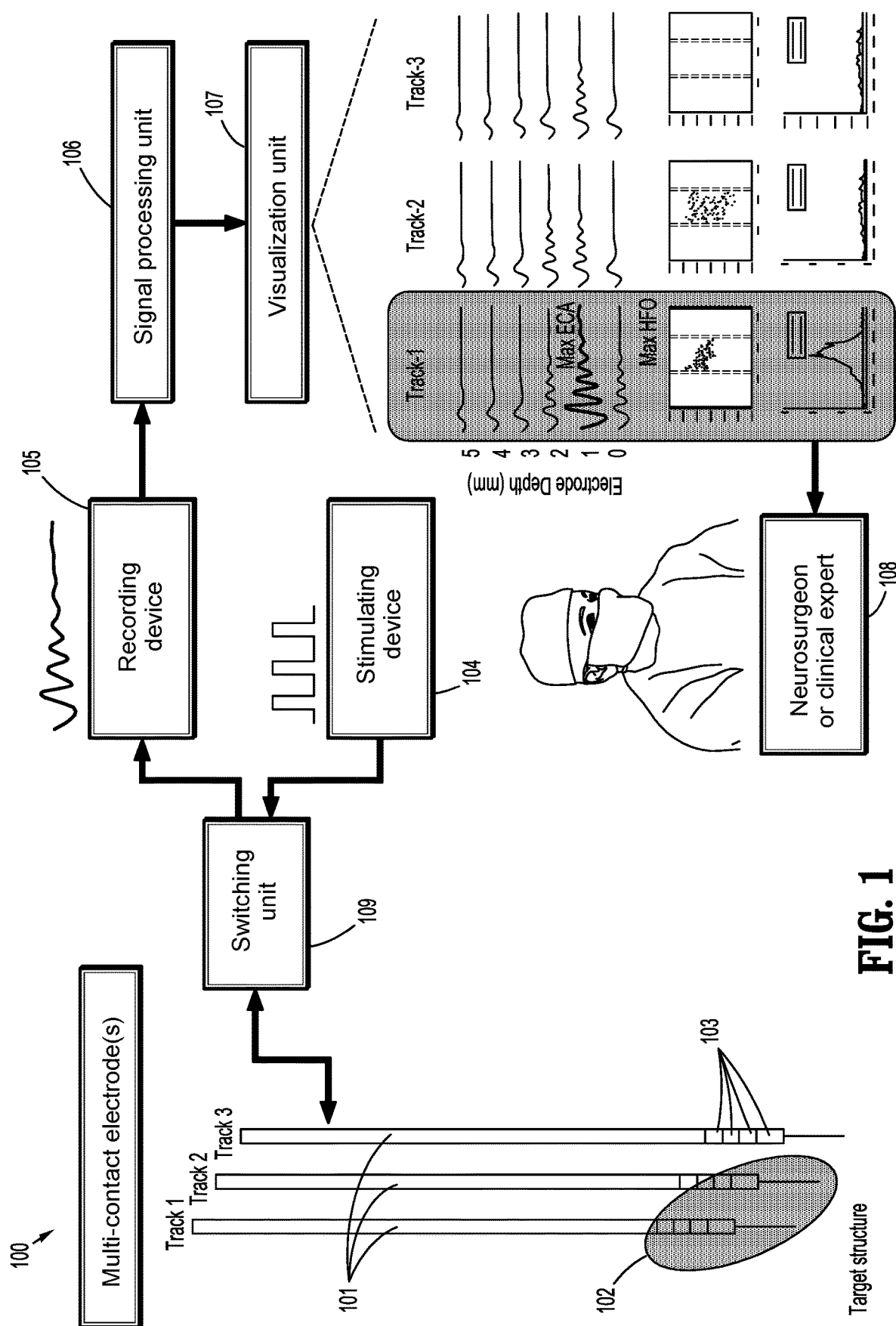
FIG. 1 is a block diagram of a system for locating an implantation site in the brain according to aspects of the present disclosure.

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

In aspects of the present disclosure, modulations in local field potentials (LFP) induced by electrical stimulation of the subthalamic nucleus (STN), such as in Parkinson's disease (PD) patients, undergoing deep brain stimulation (DBS) are employed. The systems and methods describe herein optimize frequency and other parameters to increase the effectiveness of DBS by locating ideal implantation sites and calibrating treatment parameters on an individual basis. The systems and methods described herein deliver electrical stimulation to the brain and record the response of the brain before, during and after stimulation. Based on the measured electrophysiological markers in response to the stimulation, the method and system fine tunes its parameters. Since movement and other psychiatric disorders are a network disease, one advantage of the systems and methods described herein is that they probe the state of the network with stimulation and then adapt the stimulation parameters to the response signal in a closed-loop fashion.

In the STN, therapeutic high-frequency stimulation (130-180 Hz) induces high-frequency oscillations (~300 Hz, HFO) similar to those observed with pharmacological treatment. Along with HFOs, evoked compound activity (ECA) after each stimulation pulse was identified. While ECA was observed in both therapeutic and non-therapeutic (20 Hz) stimulation, the HFOs were induced only with therapeutic frequencies and the associated ECA were significantly more resonant. The relative degree of enhancement in the HFO power was related to the interaction of stimulation pulse with the phase of ECA.

High-frequency STN-DBS tunes the neural oscillations to their healthy/treated state, similar to pharmacological treatment, and the stimulation frequency to maximize these oscillations can be inferred from the phase of ECA waveforms of individual subjects. The induced HFOs can, therefore, be utilized as a marker of successful re-calibration of the dysfunctional circuit generating PD symptoms.

As described in more detail below, high-frequency stimulation (HFS) exerts its therapeutic effect by modulating oscillatory activity in the STN, similar to the effect of pharmaceutical treatment.

It is anticipated that the systems and methods described herein may be applied to movement disorders such as Parkinson's disease, essential tremor, Tourette's syndrome, epilepsy, dystonia, psychiatric/cognitive disorders such as obsessive-compulsive disorder, severe depression, Alzheimer's dementia, and bipolar disorder.

It is anticipated that the systems and methods described herein may be applied to target brain structures such as the STN, globus pallidus (internal and external), thalamus, cortex, substantia nigra (pars reticulata and pars compacta), and the pedunculopontine nucleus.

The phrase "chronic electrode" refers to a multi-contact electrode, such as a DBS electrode, that has been surgically implanted in an individual's brain. The chronic electrodes described in more detail below may each have individually activatable contacts at different locations similar to that of the multi-contact electrodes described herein. Each contact of each choric electrode/multi-contact electrode may be controlled to deliver DBS based on a variety of parameters that are specially adjusted to account for an individuals personalized brain responses.

Referring to FIG. 1, a system 100 for locating a site for electrode implantation in the brain includes a plurality of multi-contact electrodes 101. The plurality of multi-contact electrodes 101 is configured for insertion into a region of a target structure 102 in an individual's brain. Each multi-contact electrode 101 extends to a different geographic region along a distinct anatomic track (e.g., at different depths with respect to the individual's skull). A plurality of contacts 103 are spaced apart from each other along a length (e.g., along a proximal to distal length) of each multi-contact electrode 101.

A stimulating device 104 is in electrical communication with each of the plurality of multi-contact electrodes 101. The stimulating device 104 applies High Frequency Stimulation (HFS) to each of the plurality of multi-contact electrodes 101. The HFS may be greater than 100 Hz (e.g., from 100 Hz to 200 Hz).

The stimulating device 104 is configured to selectively apply the HFS to a subset of contacts 103 of one multi-contact electrode 101 of the plurality of multi-contact electrodes. A recording device 105 is configured to measure High Frequency Oscillations (HFO) evoked in the region of the target structure 102 by the HFS. The recording device 105 is configured to measure Evoked Compound Activity (ECA) evoked in the region of the target structure 102 by the HFS.

A signal processing unit 106 is in communication with the recording device 105. The signal processing unit 106 determines if at least one of the HFO and the ECA is above a predetermined threshold to identify a location of the one contact 103 of the multi-contact electrode 101 as a site for electrode implantation in the individual's brain.

A visualization unit 107 visually displays the measured HFO and ECA. The visualization unit 107 may individually display HFO or ECA evoked by each contact 103 of each multi-contact electrode 101. Thus, a neurosurgeon or clinical expert 108 can visually identify HFO/ECA evoked by each individual contact 103.

According to an aspect of the disclosure, a switching unit controls 109 the HFS applied by the stimulating device 104. If the at least one of the HFO and ECA is below the predetermined threshold, the switching unit 109 is configured to control the stimulating device 104 to apply a second HFS to a second subset of contacts 103 of the multi-contact electrode 101 of the plurality of multi-contact electrodes.

The system 100 described with reference to FIG. 1 is configured to measure HFO and ECA intraoperatively. After one or more sites for electrode implantation in the individual's brain are identified, an electrode (i.e., a chronic electrode) is surgically implanted in each of the one or more sites for long term DBS.

Figure 2:
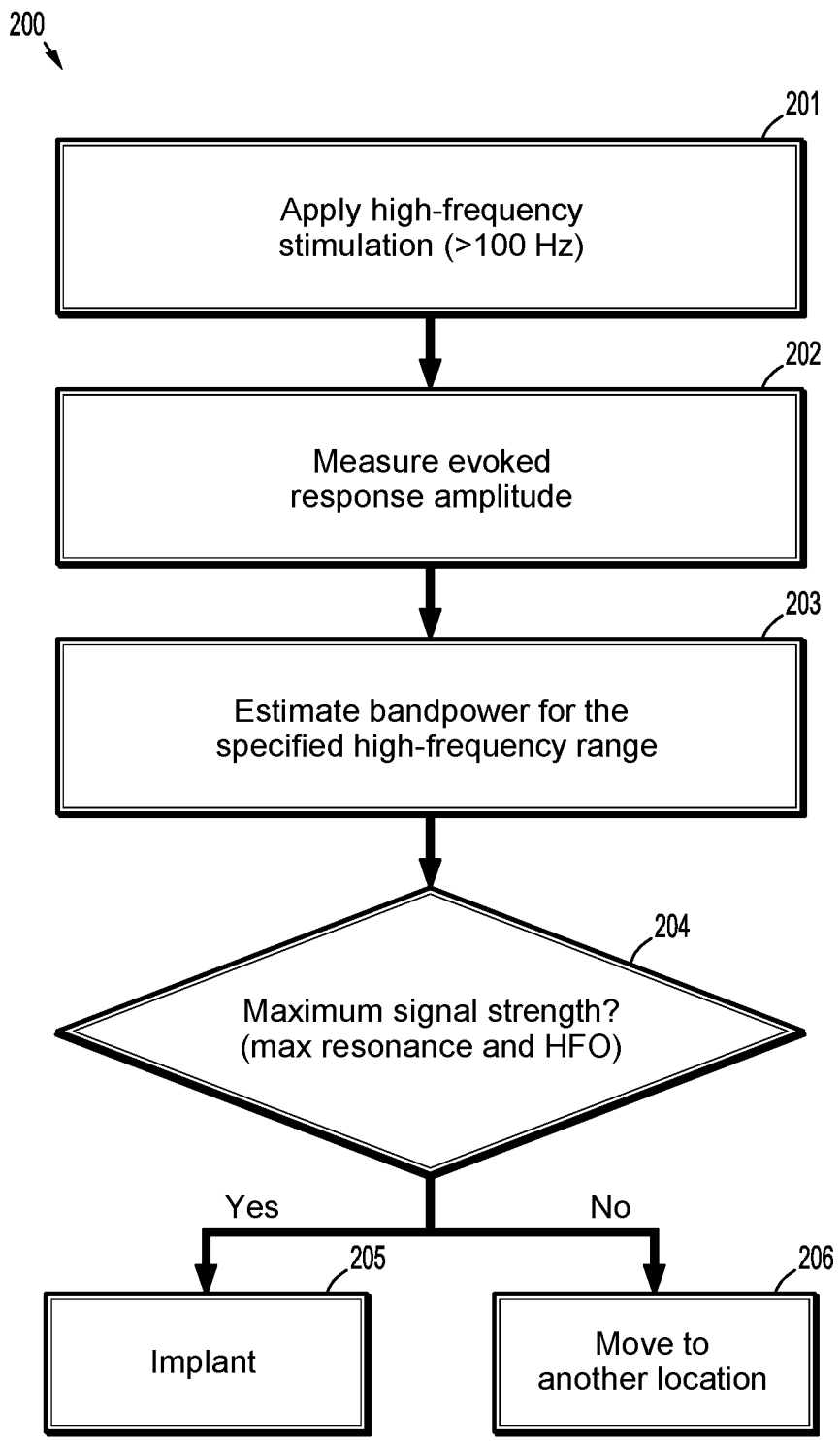
FIG. 2 is a block diagram of a method for locating an implantation site in the brain according to aspects of the present disclosure.

FIG. 2 is a block diagram of a method 200 for locating an implantation site in the brain that may be employed by the system 100.

Referring to FIG. 2, method 200 includes applying HFS (step 201), measuring evoked response amplitude (step 202) and estimating bandpower for the specified high-frequency range (step 203). The method includes determining if a maximum signal strength is received (step 204). If a maximum signal strength is received then an implant is implanted (step 205). If a maximum signal strength is not received then a decision is made to move to another location (step 206).

Figure 3:
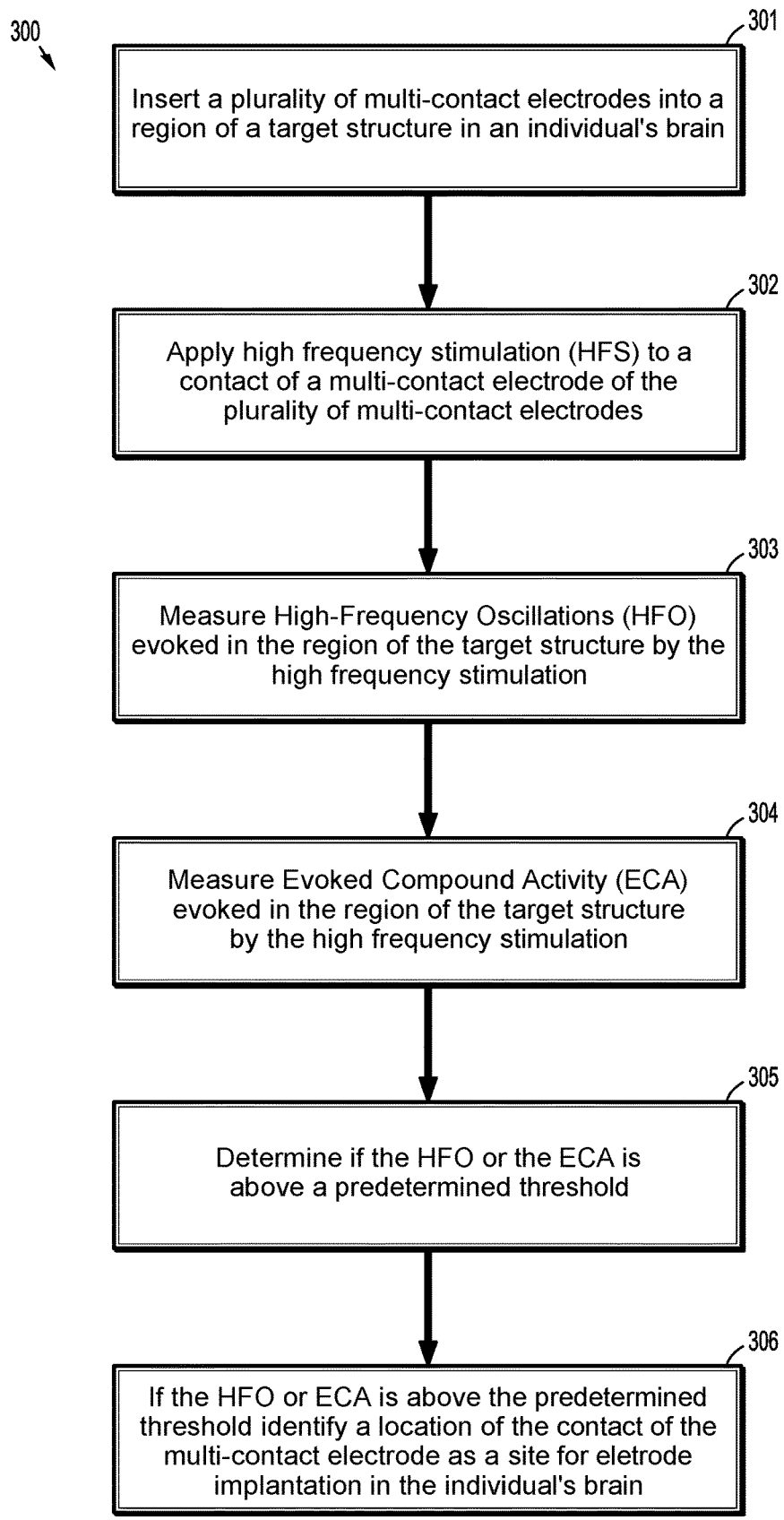
FIG. 3 is a block diagram of another method for locating an implantation site in the brain according to aspects of the present disclosure.

Referring to FIGS. 1 and 3, another method of locating an implantation site in the brain 300 that may be employed by the system 100 is described. Method 300 includes inserting a plurality of multi-contact electrodes into a region of a target structure in an individual's brain (step 301). The multi-contact electrodes can be extended through burr hole formed in the individual's skull.

HFS is applied to a contact of a multi-contact electrode of the plurality of multi-contact electrodes (step 302). High Frequency Oscillations (HFO) evoked in the region of the target structure by the HFS are measured (step 303). Evoked Compound Activity (ECA) evoked in the region of the target structure by the HFS is measured (step 304). It is determined if at least one of the HFO and the ECA is above a predetermined threshold (step 305). If at least one of the HFO and the ECA is above the predetermined threshold, a location of the contact of the multi-contact electrode is identified as a site for electrode implantation in the individual's brain (step 306).

Each multi-contact electrode 101 may extend along a distinct anatomic track and distal-ends thereof may end at various depths within an individual's brain. Each multi-contact electrode 101 may include numerous contacts 103 positioned along a length thereof. Each contact 103 may selectively and individually receive an electrical stimulation (LFS or HFS) to test various depths along various tracks of the user's brain. Thus, by individually applying electrical stimulation intraoperatively, an ideal track and an ideal depth may be identified. For example, with reference to FIG. 1, Track 3 may entirely miss the target structure, Track 2 may align with a periphery of the target structure, while Track 3 aligns with a central region of the target structure. Further, a distal-most contact (i.e., contact 1) of Track 1 may evoke a maximum ECA and HFO. Thus, the position of contact 1, along the Track 1 multi-contact electrode would be identified as a desired site for electrode implantation in an individual's brain. The implanted electrode, as described in more detail below, can then be calibrated by adjusting the specific parameters thereof, to maximize effectiveness of DBS on an individual basis. As described in more detail below, parameter adjustments can be made to account for an individual's personalized brain response and underlying structural or electrochemical variations. The combination of idealized electrode placement and idealized parameter settings maximizes treatment effectiveness of DBS. Further, the parameter adjustments can be periodically adjusted to account for changes within an individual's underlying disease state progression, anatomical changes occurring over time, or electrochemical changes occurring over time.

If the HFO or the ECA is below the predetermined threshold, a second high frequency stimulation is applied to a second subset of contacts of the multi-contact electrode of the plurality of multi-contact electrodes. If no site for electrode implantation in the individual's brain is identified, the plurality of multi-contact electrodes is moved to a second region in the individual's brain. For example, If none of the multi-contact electrodes are found to evoke a suprathreshold HFO or ECA, the multi-contact electrodes can be advanced further into the individual's brain on a millimeter by millimeter basis until a desired HFO/ECA is evoked by at least one contact.

In an aspect of the present disclosure, the HFS is greater than 100 Hz.

In an aspect of the present disclosure, the HFO includes an oscillation pattern between 200-450 Hz.

In an aspect of the present disclosure, the ECA includes a resonance pattern above a predetermined threshold (see, e.g., FIG. 11 described in more detail below).

Figure 4:
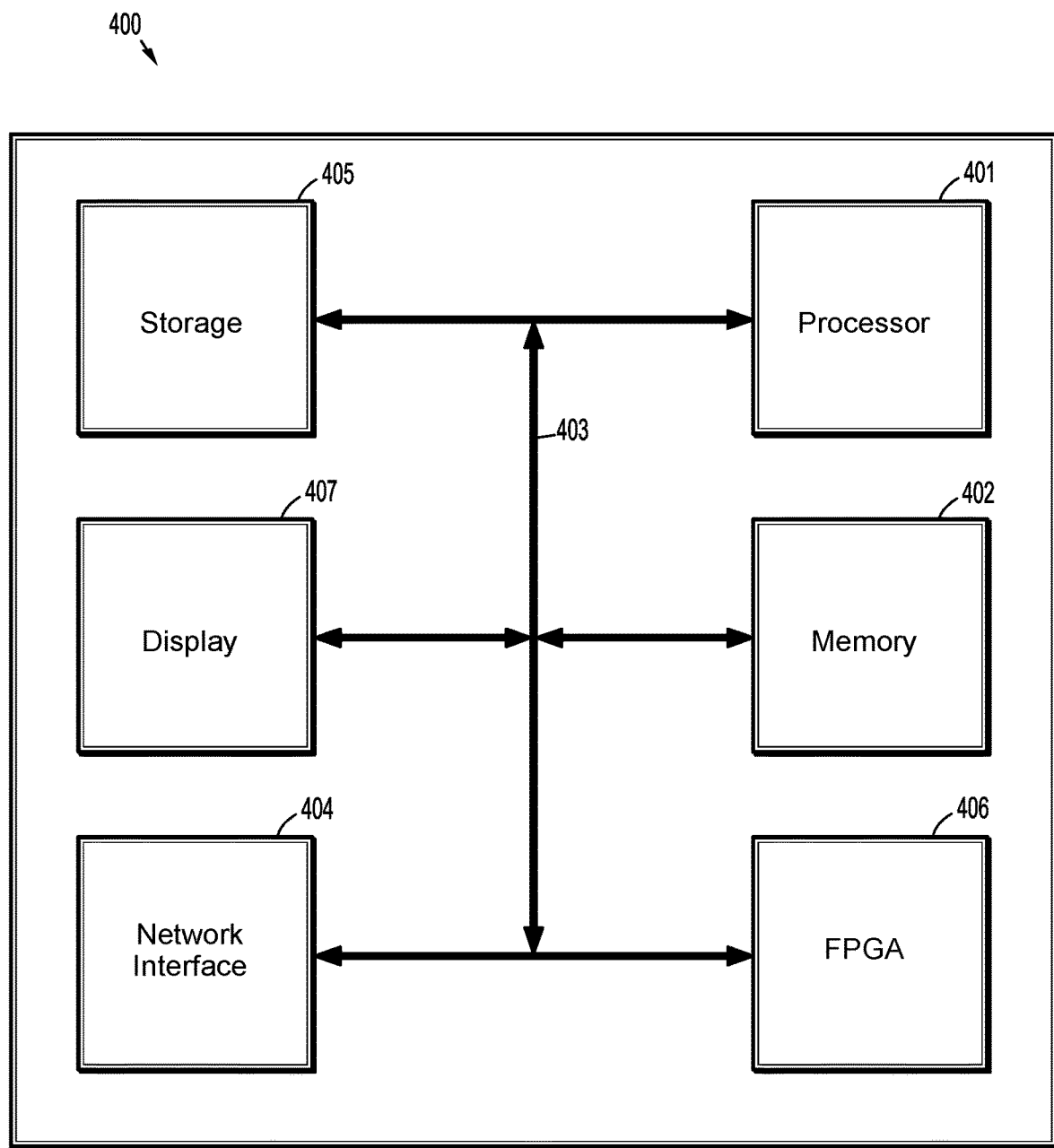
FIG. 4 is a block diagram of an exemplary computer of a signal processing unit according to aspects of the present disclosure.

FIG. 4 is a block diagram of an exemplary computer 400 of a signal processing unit 106 of FIG. 1 according to an aspect of the present disclosure.

Referring to FIG. 4, the signal processing unit 106 may include a processor 401 connected to a computer-readable storage medium or a memory 402 which may be a volatile type memory, e.g., RAM, or a non-volatile type memory, e.g., flash media, disk media, etc. The processor 401 may be another type of processor such as, without limitation, a digital signal processor, a microprocessor, an ASIC, a graphics processing unit (GPU), field-programmable gate array (FPGA), or a central processing unit (CPU).

In some aspects of the disclosure, the memory 402 can be random access memory, read-only memory, magnetic disk memory, solid state memory, optical disc memory, and/or another type of memory. The memory 402 can communicate with the processor 401 through communication buses 403 of a circuit board and/or through communication cables such as serial ATA cables or other types of cables. The memory 402 includes computer-readable instructions that are executable by the processor 401 to operate the signal processing unit 106. The signal processing unit 106 may include a network interface 404 to communicate with other computers or a server. A storage device 405 may be used for storing data. The signal processing unit 106 may include one or more FPGAs 406. The FPGA 406 may be used for executing various machine learning algorithms. A display 407 may be employed to display data processed by the signal processing unit 106.

The signal processing unit 106 described with reference to FIGS. 1 and 4 is substantially the same as the signal processing unit 506 described with reference to FIG. 5 below unless otherwise indicated, and thus duplicative descriptions may be omitted herein. For example, the signal processing unit 506 illustrated in FIG. 5 may have substantially the same hardware configuration as that of the signal processing unit 106 illustrated in FIG. 1. The switching unit 509, recording device 505, and stimulating device 504 described with reference to FIG. 5 below are substantially the same as the switching unit 109, recording device 105, and stimulating device 104 described with reference to FIGS. 1 to 3 unless otherwise indicated, and thus duplicative descriptions may be omitted herein.

Figure 5:
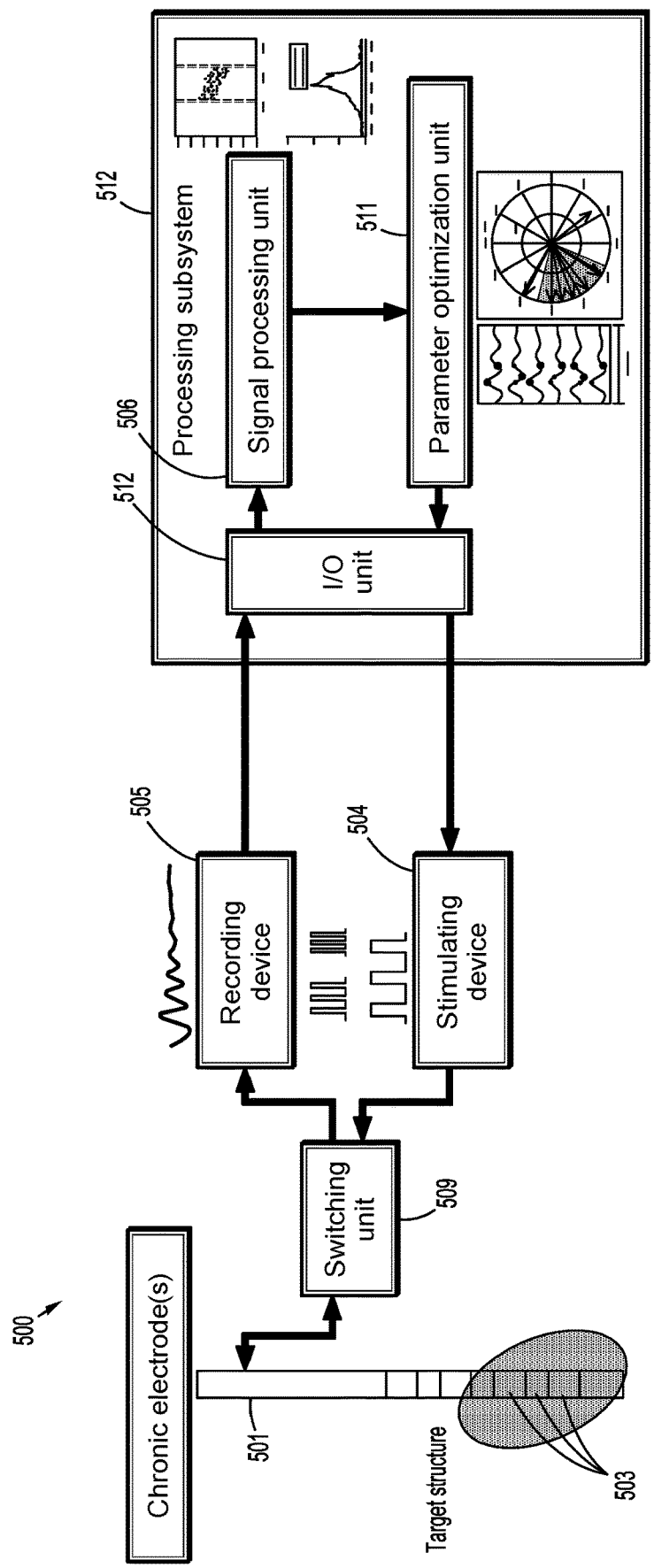
FIG. 5 is a block diagram of an implantable system for determining DBS parameters according to aspects of the present disclosure.

Referring to FIG. 5, a system 500 for determining deep brain stimulation parameters includes at least one multi-contact electrode 501 configured for implanting in a target structure 502 in an individuals' brain. The multi-contact electrode 501 may be a chronically implanted electrode, as described in more detail below. The stimulating device 504 is in electrical communication with the at least one multi-contact electrode 501. The stimulating device 504 is configured to apply Low Frequency Stimulation (LFS) (e.g., less than 105 Hz) or High Frequency Stimulation (HFS) (e.g., from 100 Hz to 200 Hz) to the at least one multi-contact electrode 501.

According to an aspect of the disclosure, the switching unit 509 controls the HFS applied by the stimulating device 504. If the at least one of the HFO and ECA is below the predetermined threshold, the switching unit 509 is configured to control the stimulating device 504 to apply a second HFS to a second subset of contacts 503 of the multi-contact electrode 501 of the plurality of multi-contact electrodes.

The recording device 505 is configured to record at least one of Evoked Compound Activity (ECA) evoked in the target structure 502 by the LFS and High Frequency Oscillations (HFO) evoked in the target structure 502 by the HFS. The signal processing unit 506 is in communication with the recording device 505. The signal processing unit 506 determines a range of frequencies for delivering brain stimulation within a predetermined range based on a phase space extracted from the ECA (see, e.g., FIG. 11). The signal processing unit 506 analyzes High Frequency Oscillations (HFO) evoked in the target structure 502 by the applied stimulation frequencies within the determined range. A parameter optimization unit 511 determines a frequency evoking HFO above a predetermined threshold, and selects the frequency as a treatment frequency for the target structure.

The stimulating device 504 is configured to selectively apply the LFS or HFS to one contact 503 of one multi-contact electrode 501.

In an aspect of the present disclosure, an input/output (I/O) unit 512 is in electrical communication with the stimulating device 504, the recording device 505, the signal processing unit 506, and the parameter optimization unit 511.

At least one of the stimulating device 504, the recording device 505, the signal processing unit 506, and the parameter optimization unit 511 are implanted in the individual's chest. For example, a processing subsystem 512 including the signal processing unit 506, the parameter optimization unit 511 and the I/O unit 512 may be implanted in the patient's chest.

The processing subsystem 512 can control the implanted multi-contact electrodes 501 for DBS.

Figure 6:
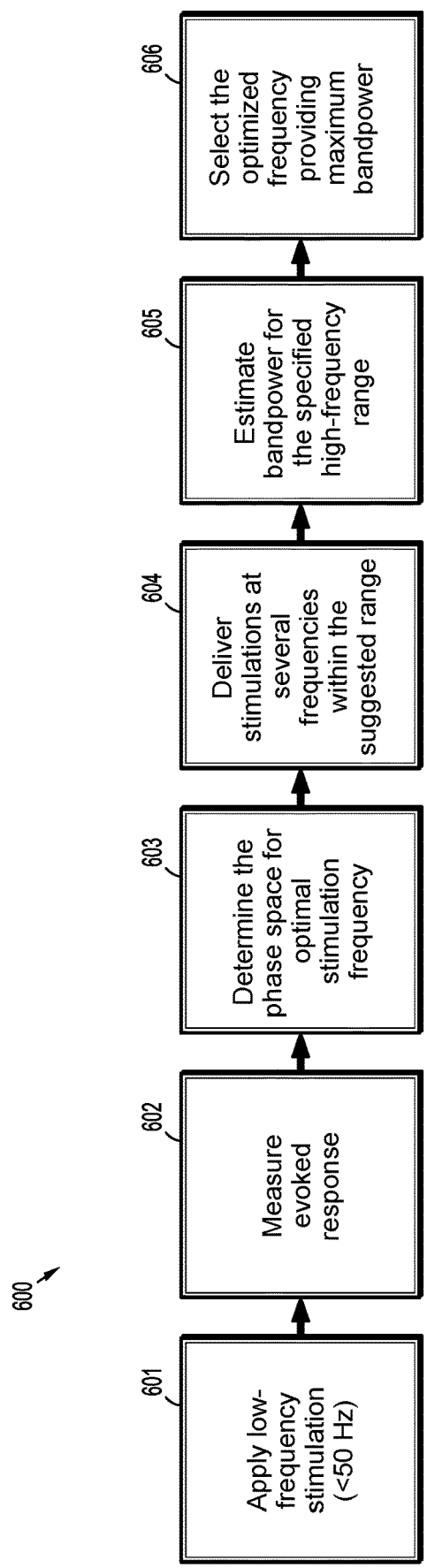
FIG. 6 is a block diagram of a method for determining DBS parameters according to aspects of the present disclosure.
Figure 7:
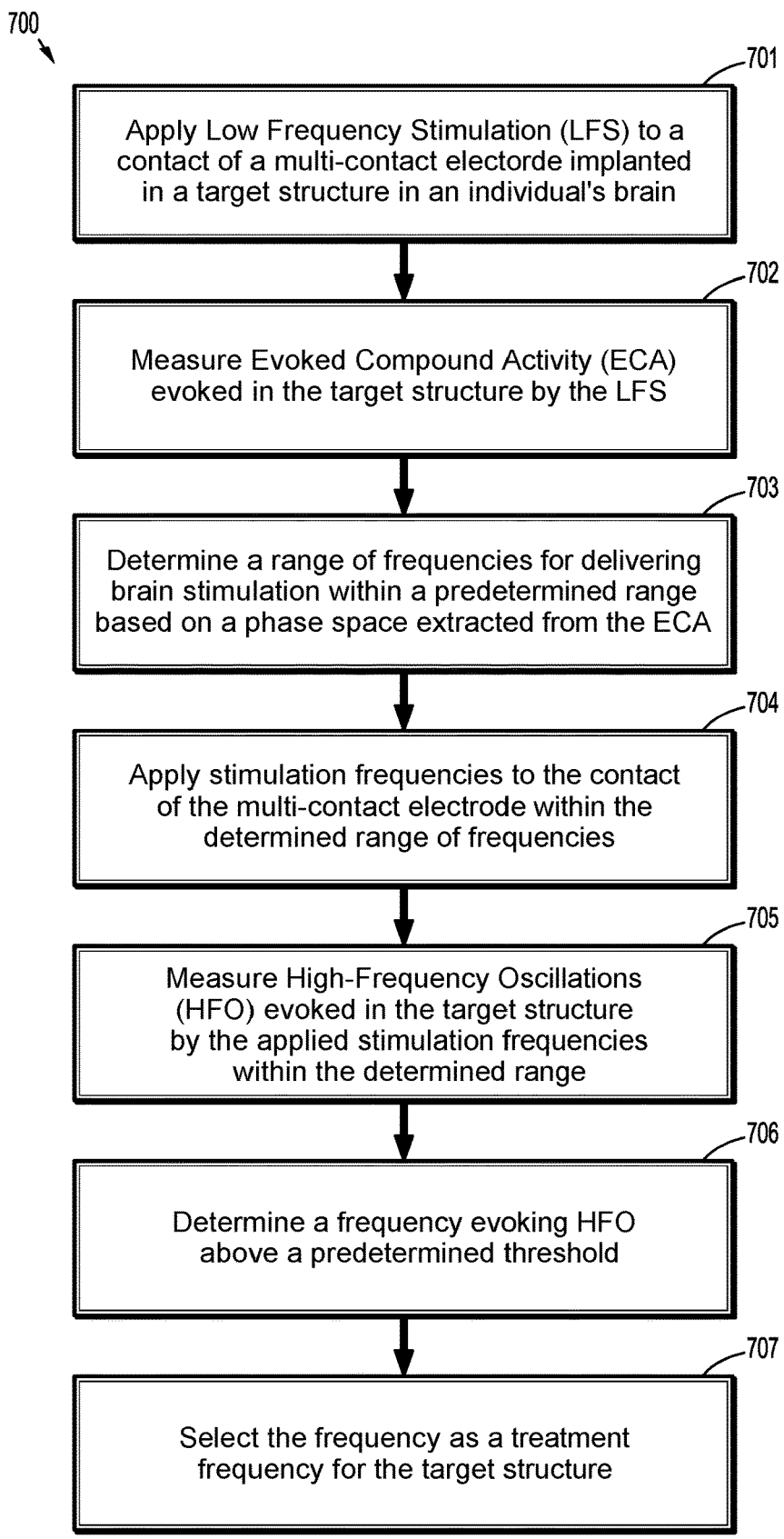
FIG. 7 is a block diagram of another method for determining DBS parameters according to aspects of the present disclosure.

Referring to FIGS. 5 to 7, a method of determining brain stimulation parameters includes applying Low Frequency Stimulation (LFS) (e.g., less than 105 Hz) to a contact of a multi-contact electrode implanted in a target structure in an individual's brain. Evoked Compound Activity (ECA) evoked in the target structure by the LFS is measured.

A range of frequencies for delivering brain stimulation within a predetermined range based on a phase space extracted from the ECA is determined. Stimulation frequencies are applied to the contact of the multi-contact electrode within the determined range of frequencies. High Frequency Oscillations (HFO) of Local Field Potentials evoked in the target structure by the applied stimulation frequencies within the determined range are measured. A frequency evoking HFO above a predetermined threshold is determined. The determined frequency is selected as a treatment frequency for the target structure.

In an aspect of the present disclosure, the selected frequency is greater than 130 Hz.

In an aspect of the present disclosure, the selected frequency is about 130 Hz, about 160 Hz, or about 180 Hz and can be any frequency between 100-200 Hz.

In an aspect of the present disclosure, the measured HFO evoked in the target structure is between 200-450 Hz.

In an aspect of the present disclosure, the ECA includes a resonating response above a predetermined threshold.

If the ECA is below a predetermined threshold, a second LFS is applied to a second subset of contacts of the multi-contact electrode in a different location within the target structure than the contact of the multi-contact electrode.

As an example, one or more chronic electrodes with multiple contacts are implanted during the intraoperative procedure. A low frequency (<105 Hz) stimulation is applied through one or more contacts. An ECA waveform in Local Field Potential is recorded and its characteristics (e.g., amplitude, phase, resonance duration) are determined. The stimulation frequency range for the optimal response is then computed based on phase space extracted from ECA. Stimulation is delivered at frequencies within this range and the corresponding HFO frequency and/or power is computed. The frequency associated with the maximum HFO power is selected for treatment. Thus, the system and methods described herein can be employed to fine tune stimulation frequency by processing HFO power and ECA phase space.

The systems and methods described with reference to FIGS. 5 to 7 may periodically be employed to recalibrate the brain stimulation parameters, such as on a predetermined schedule (e.g., once every twenty four hours, once weekly, etc.). In addition to periodically recalibrating treatment parameters, recalibration may also be performed autonomously to dynamically optimize treatment parameters based on personalized and individual physiological changes that occur over time, without the need for direct intervention by a neurosurgeon or treatment expert.

Referring particularly to FIG. 6, a method for determining DBS parameters 600 includes applying LFS (step 601), measuring evoked response (step 602), determining the phase space for optical stimulation frequency (step 603), delivering stimulations at several frequencies within the suggested range (step 604), estimating bandpower for the specified high-frequency range (step 605), and selecting the optimized frequency providing maximum bandpower (step 606).

Referring to FIG. 7, another method for determining DBS parameters 700 includes applying LFS to a contact of a multi-contact electrode implanted in a target structure in an individual's brain (step 701). Method 700 includes measuring ECA evoked in the target structure by the LFS (step 702) and determining a range of frequencies for delivering brain stimulation within a predetermined range based on a phase space extracted from the ECA (step 703). Method 700 includes applying stimulation frequencies to the contact of the multi-contact electrode within the determined range of frequencies (step 704) and measuring HFO evoked in the target structure by the applied stimulation frequencies within the determined range (step 705). Method 700 includes determining a frequency evoking HFO above a predetermined threshold (step 706) and selecting the frequency as a treatment frequency for the target structure (step 707).

Figure 8:
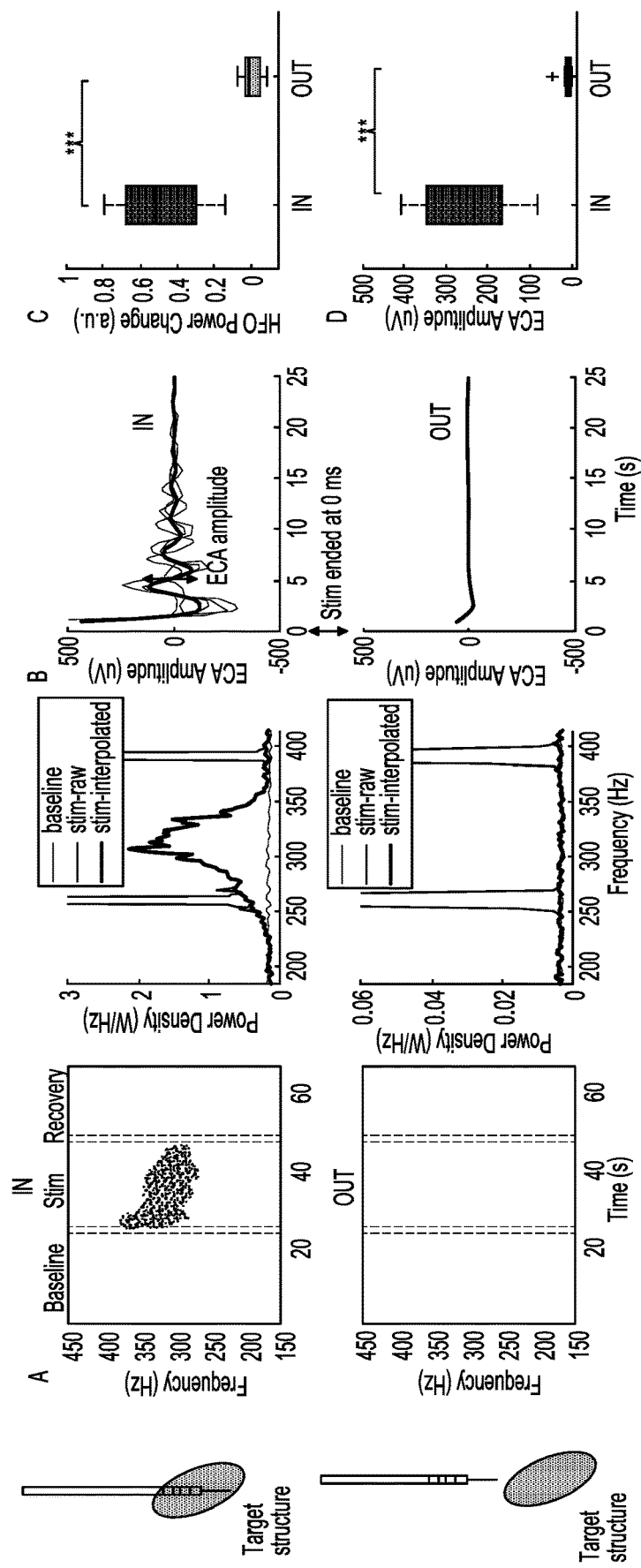
FIG. 8 displays recorded HFO evoked in the STN when a multi-contact electrode is positioned in the STN and an absence of HFO when the multi-contact electrode is not positioned in the STN.

FIG. 8 displays recorded HFO evoked in the STN when a multi-contact electrode is positioned in the STN and an absence of HFO when the multi-contact electrode is not positioned in the STN. Referring to FIG. 8, HFO and resonant evoked compound activity (ECA) are observed during high-frequency DBS only in the STN. In 10 hemispheres, 130 Hz stimulation was performed out- and in-STN to identify and rule out the possible artifacts that might have been caused by the stimulation or the recording hardware.

Figure 9:
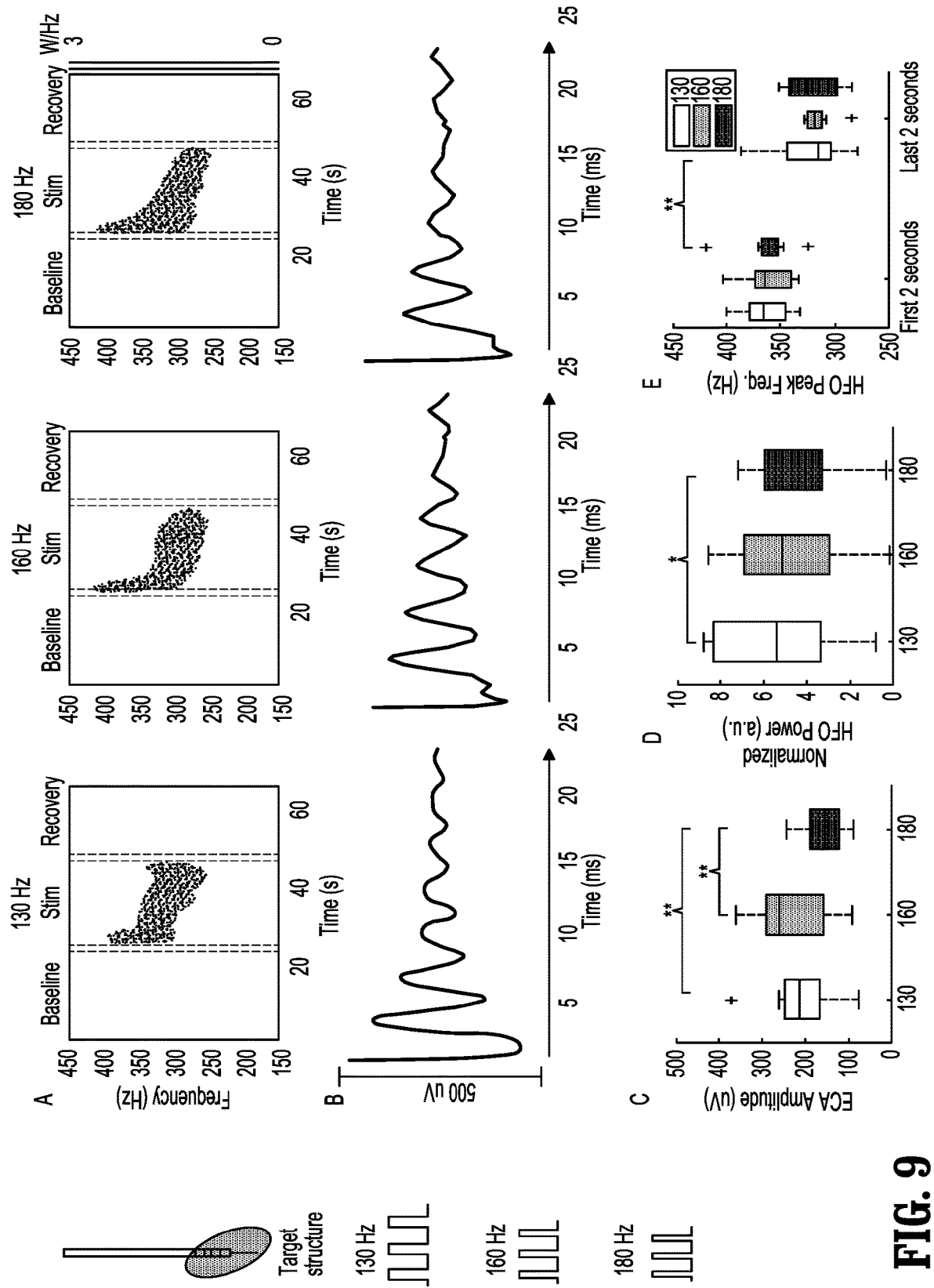
FIG. 9 displays recorded HFO and ECA at various HFS frequencies when the multi-contact electrode is positioned in the STN.

FIG. 9 displays recorded HFO and ECA at various HFS frequencies when the multi-contact electrode is positioned in the STN. Referring to FIG. 9, High-frequency stimulations (e.g., 130 Hz, 160 Hz, and 180 Hz) modulate HFO and ECA in different amplitudes.

Figure 10:
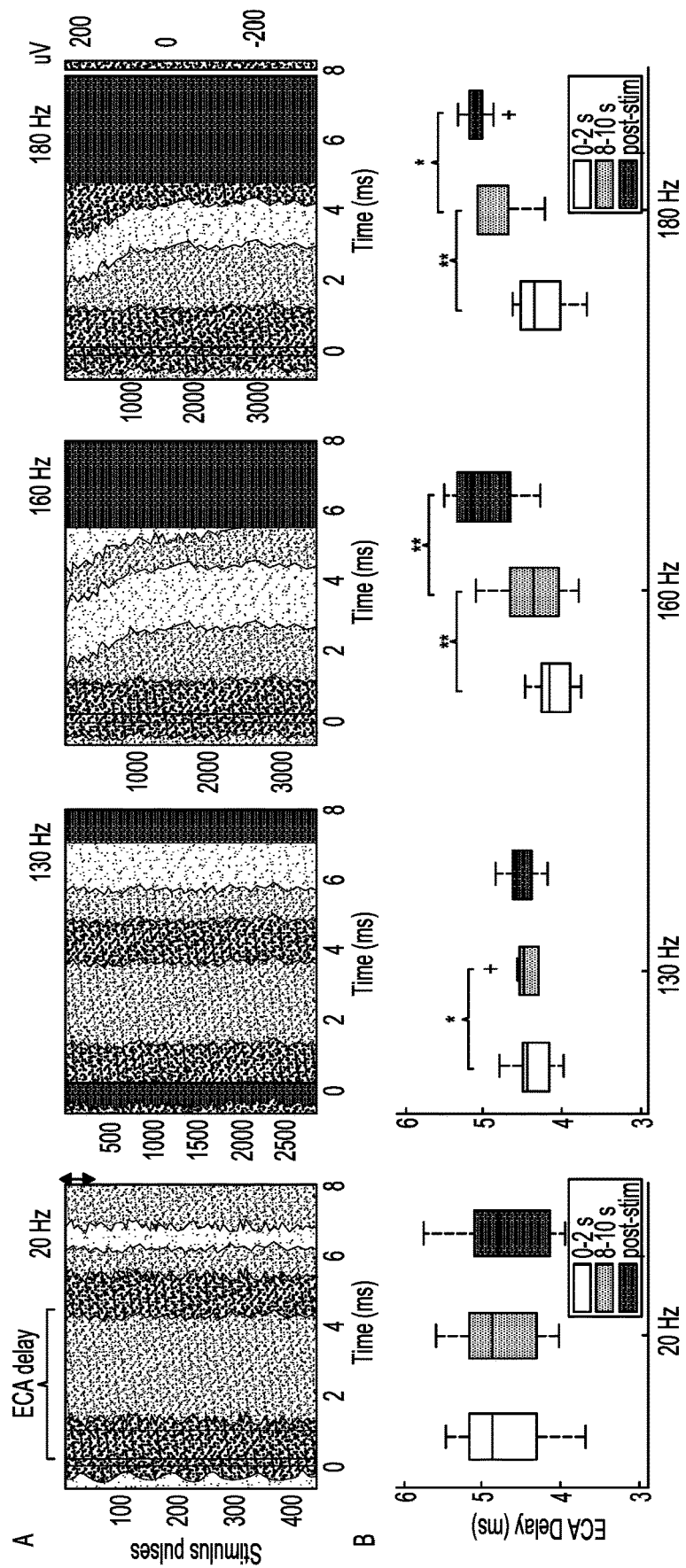
FIG. 10 displays recorded ECA for a LFS frequency compared with various HFS frequencies.

FIG. 10 displays recorded ECA for a LFS frequency compared with various HFS frequencies. Referring to FIG. 10, inter-pulse evoked activity shows adaptation only with high-frequency stimulation (e.g., 130 Hz, 160 Hz, and 180 Hz), and not with low frequency stimulation (e.g., 20 Hz).

Figure 11:
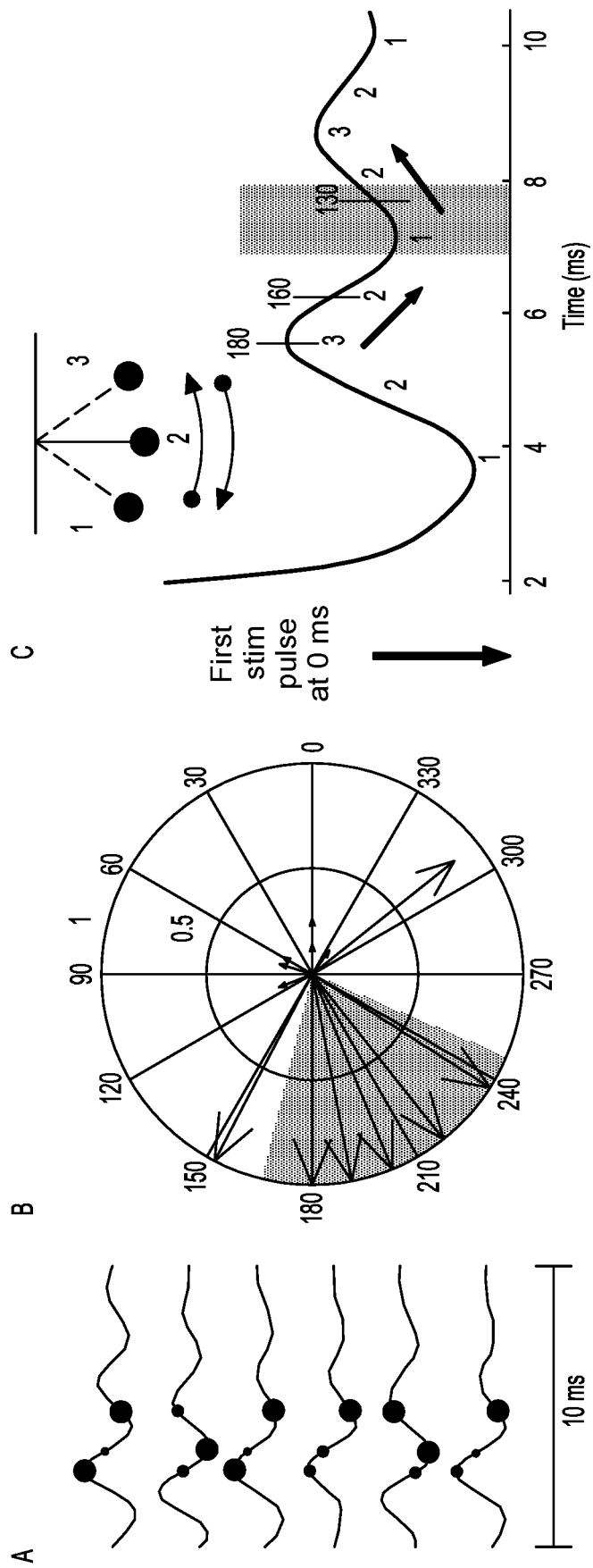
FIG. 11 illustrates DBS tuning of various HFS frequencies based on a phase of an ECA waveform.

FIG. 11 illustrates DBS tuning of various HFS frequencies based on a phase of an ECA waveform. Referring to FIG. 11, the DBS can be tuned to provide maximum modulatory effect based on the phase of ECA waveform.

Each of the following references is incorporated by reference herein in its entirety.

Agnesi, F., Connolly, A. T., Baker, K. B., Vitek, J. L., and Johnson, M. D. (2013). Deep Brain Stimulation Imposes Complex Informational Lesions. *PLoS One* 8, 1-11. doi: 10.1371/journal.pone.0074462.

Ashby, P., Paradiso, G., Saint-Cyr, J. A., Chen, R., Lang, A. E., and Lozano, A. M. (2001). Potentials recorded at the scalp by stimulation near the human subthalamic nucleus. *Clin Neurophysiol* 112, 431-437. doi:10.1016/S1388-2457(00)00532-0.

Benabid, A. L., Chabardes, S., Mitrofanis, J., and Pollak, P. (2009). Deep brain stimulation of the subthalamic nucleus for the treatment of Parkinson's disease. *Lancet Neurol*, 67-81.

Benazzouz, A., Gao, D., Ni, Z., Piallat, B., Bouali-Benazzouz, R., and Benabid, A. (2000). Effect of high-frequency stimulation of the subthalamic nucleus on the neuronal activities of the substantia nigra pars reticulata and ventrolateral nucleus of the thalamus in the rat. *Neuroscience* 99, 289-295. doi:10.1016/S0306-4522(00)00199-8.

Berens, P. (2009). CircStat: A MATLAB Toolbox for Circular Statistics. *J Stat Softlw* 31, 293-295. doi:10.18637/jss.v031.i10.

Bergman, H., Wichmann, T., Karmon, B., and DeLong, M. R. (1994). The primate subthalamic nucleus. II. Neuronal activity in the MPTP model of parkinsonism. *J Neurophysiol* 72, 507-20. doi:10.1152/jn.1994.72.2.507.

Bevan, M. D., Magill, P. J., Terman, D., Bolam, J. P., and Wilson, C. J. (2002). Move to the rhythm: oscillations in the subthalamic nucleus-external globus pallidus network. *Trends Neurosci* 25, 525-31. doi:10.1016/s0166-2236(02)02235-x.

Brittain, J.-S., and Brown, P. (2014). Oscillations and the basal ganglia: Motor control and beyond. *Neuroimage* 85, 637-647. doi:10.1016/j.neuroimage.2013.05.084.

Brown, P., Mazzone, P., Oliviero, A., Altibrandi, M. G., Pilato, F., Tonali, P. A., et al. (2004). Effects of stimulation of the subthalamic area on oscillatory pallidal activity in Parkinson's disease. *Exp Neurol* 188, 480-490. doi:10.1016/j.expneurol.2004.05.009.

Chu, H.-Y., McIver, E. L., Kovaleski, R. F., Atherton, J. F., and Bevan, M. D. (2017). Loss of Hyperdirect Pathway Cortico-Subthalamic Inputs Following Degeneration of Midbrain Dopamine Neurons. *Neuron* 95, 1306-1318.e5. doi:10.1016/j.neuron.2017.08.038.

Cleary, D. R., Raslan, A. M., Rubin, J. E., Bahgat, D., Viswanathan, A., Heinricher, M. M., et al. (2013). Deep brain stimulation entrains local neuronal firing in human globus pallidus internus. *J Neurophysiol* 109, 978-987. doi:10.1152/jn.00420.2012.

Dostrovsky, J. O., Levy, R., Wu, J. P., Hutchison, W. D., Tasker, R. R., and Lozano, A. M. (2000). Microstimulation-Induced Inhibition of Neuronal Firing in Human Globus Pallidus. *J Neurophysiol* 84, 570-574. doi:10.1152/jn.2000.84.1.570.

Erwin, B., Jr, M. M., and Baker, K. K. (2000). Mechanisms of deep brain stimulation and future technical developments. *Neurol Res* 22, 259-266. doi:10.1080/01616412.2000.11740668.

Escobar, D., Johnson, L. A., Nebeck, S. D., Zhang, J., Johnson, M. D., Baker, K. B., et al. (2017). Parkinsonism and Vigilance: Alteration in neural oscillatory activity and phase-amplitude coupling in the basal ganglia and motor cortex. *J Neurophysiol* 118, jn.00388.2017. doi:10.1152/jn.00388.2017.

Eusebio, A., Chen, C. C., Lu, C. S., Lee, S. T., Tsai, C. H., Limousin, P., et al. (2008). Effects of low-frequency stimulation of the subthalamic nucleus on movement in Parkinson's disease. *Exp Neurol* 209, 125-130. doi:10.1016/j.expneurol.2007.09.007.

Eusebio, A., Thevathasan, W., Doyle Gaynor, L., Pogosyan, A., Bye, E., Foltynie, T., et al. (2011). Deep brain stimulation can suppress pathological synchronisation in parkinsonian patients. *J Neurol Neurosurg Psychiatry* 82, 569-573. doi:10.1136/jnnp.2010.217489.

Filali, M., Hutchison, W. D., Palter, V. N., Lozano, A. M., and Dostrovsky, J. O. (2004). Stimulation-induced inhibition of neuronal firing in human subthalamic nucleus. *Exp Brain Res* 156, 274-281. doi:10.1007/s00221-003-1784-y.

Foffani, G., Ardolino, G., Egidi, M., Caputo, E., Bossi, B., and Priori, A. (2006). Subthalamic oscillatory activities at beta or higher frequency do not change after high-frequency DBS in Parkinson's disease. *Brain Res Bull* 69, 123-130. doi:10.1016/j.brainresbull 0.2005.11.012.

Foffani, G., Priori, A., Egidi, M., Rampini, P., Tamma, F., Caputo, E., et al. (2003). 300-Hz subthalamic oscillations in Parkinson's disease. *Brain* 126, 2153-2163. doi:10.1093/brain/awg229.

Fogelson, N., Kühn, A. A., Silberstein, P., Limousin, P. D., Hariz, M., Trottenberg, T., et al. (2005). Frequency dependent effects of subthalamic nucleus stimulation in Parkinson's disease. *Neurosci Lett* 382, 5-9. doi:10.1016/j.neulet.2005.02.050.

Garcia, L., D'Alessandro, G., Bioulac, B., and Hammond, C. (2005a). High-frequency stimulation in Parkinson's disease: more or less? *Trends Neurosci* 28, 209-216. doi:10.1016/j.tins.2005.02.005.

Garcia, L., D'Alessandro, G., Fernagut, P., Bioulac, B., and Hammond, C. (2005b). Impact of High-Frequency Stimulation Parameters on the Pattern of Discharge of Subthalamic Neurons. *J Neurophysiol* 94, 3662-3669. doi:10.1152/jn.00496.2005.

Gmel, G. E., Obradovic, M., Gorman, R. B., Single, P. S., Parker, J. L., Hamilton, T. J., et al. (2015). A new biomarker for subthalamic deep brain stimulation for patients with advanced Parkinson's disease—A pilot study. *J Neural Eng* 12. doi:10.1088/1741-2560/12/6/066013.

Grill, W. M., Snyder, A. N., and Miocinovic, S. (2004). Deep brain stimulation creates an informational lesion of the stimulated nucleus. *Neuroreport* 15, 1137-1140. doi:10.1097/00001756-200405190-00011.

Gross, R. E., Krack, P., Rodriguez-Oroz, M. C., Rezai, A. R., and Benabid, A.-L. (2006). Electrophysiological mapping for the implantation of deep brain stimulators for Parkinson's disease and tremor. *Mov Disord* 21, S259-S283. doi:10.1002/mds.20960.

Guo, Y., Rubin, J. E., McIntyre, C. C., Vitek, J. L., and Terman, D. (2008). Thalamocortical Relay Fidelity Varies Across Subthalamic Nucleus Deep Brain Stimulation Protocols in a Data-Driven Computational Model. *J Neurophysiol* 99, 1477-1492. doi:10.1152/jn.01080.2007.

Hahn, P. J., Russo, G. S., Hashimoto, T., Miocinovic, S., Xu, W., McIntyre, C. C., et al. (2008). Pallidal burst activity during therapeutic deep brain stimulation. *Exp Neurol* 211, 243-251. doi:10.1016/j.expneurol.2008.01.032.

Hashimoto, T., Elder, C. M., Okun, M. S., Patrick, S. K., and Vitek, J. L. (2003). Stimulation of the Subthalamic Nucleus Changes the Firing Pattern of Pallidal Neurons. *J Neurosci* 23, 1916-1923. doi:10.1523/JNEUROSCI.23-05-01916.2003.

Herrington, T. M., Cheng, J. J., and Eskandar, E. N. (2016). Mechanisms of deep brain stimulation. *J Neurophysiol* 115, 19-38. doi:10.1152/jn.00281.2015.

Hoang, K. B., and Turner, D. A. (2019). The Emerging Role of Biomarkers in Adaptive Modulation of Clinical Brain Stimulation. *Neurosurgery* 85, E430-E439. doi:10.1093/neuros/nyz096.

Huang, H., Watts, R. L., and Montgomery, E. B. (2014). Effects of deep brain stimulation frequency on bradykinesia of Parkinson's disease. *Mov Disord* 29, 203-206. doi:10.1002/mds.25773.

Johnson, M. D., Miocinovic, S., McIntyre, C. C., and Vitek, J. L. (2008). Mechanisms and targets of deep brain stimulation in movement disorders. *Neurotherapeutics* 5, 294-308. doi:10.1016/j.nurt.2008.01.010.

Kaku, H., Ozturk, M., Viswanathan, A., Shahed, J., Sheth, S. A., Kumar, S., et al. (2020). Unsupervised clustering reveals spatially varying single neuronal firing patterns in the subthalamic nucleus of patients with Parkinson's disease. *Clin Park Relat Disord* 3, 100032. doi:10.1016/j.prdoa.2019.100032.

Kane, A., Hutchison, W. D., Hodaie, M., Lozano, A. M., and Dostrovsky, J. O. (2009). Dopamine-dependent high-frequency oscillatory activity in thalamus and subthalamic nucleus of patients with Parkinson's disease. *Neuroreport* 20, 1549-1553. doi:10.1097/WNR.0b013e32833282c8.

Kent, A. R., Swan, B. D., Brocker, D. T., Turner, D. A., Gross, R. E., and Grill, W. M. (2015). Measurement of Evoked Potentials During Thalamic Deep Brain Stimulation. *Brain Stimul* 8, 42-56. doi:10.1016/j.brs.2014.09.017.

Kita, H., and Kitai, S. T. (1991). Intracellular study of rat globus pallidus neurons: membrane properties and responses to neostriatal, subthalamic and nigral stimulation. *Brain Res* 564, 296-305. doi:10.1016/0006-8993(91)91466-E.

Kühn, A. A., Kempf, F., Brucke, C., Gaynor Doyle, L., Martinez-Torres, I., Pogosyan, A., et al. (2008). High-Frequency Stimulation of the Subthalamic Nucleus Suppresses Oscillatory Activity in Patients with Parkinson's Disease in Parallel with Improvement in Motor Performance. *J Neurosci* 28, 6165-6173. doi:10.1523/JNEUROSCI.0282-08.2008.

Kuhn, A. A., Williams, D., Kupsch, A., Limousin, P., Hariz, M., Schneider, G., et al. (2004). Event-related beta desynchronization in human subthalamic nucleus correlates with motor performance. *Brain* 127, 735-746. doi:10.1093/brain/awh106.

Kuncel, A. M., Cooper, S. E., Wolgamuth, B. R., and Grill, W. M. (2007). Amplitude- and Frequency-Dependent Changes in Neuronal Regularity Parallel Changes in Tremor With Thalamic Deep Brain Stimulation. *IEEE Trans Neural Syst Rehabil Eng* 15, 190-197. doi:10.1109/TNSRE.2007.897004.

Leventhal, D. K., Gage, G. J., Schmidt, R., Pettibone, J. R., Case, A. C., and Berke, J. D. (2012). Basal ganglia beta oscillations accompany cue utilization. *Neuron* 73, 523-536. doi:10.1016/j.neuron.2011.11.032.

Li, Q., Ke, Y., Chan, D. C. W., Qian, Z. M., Yung, K. K. L., Ko, H., et al. (2012). Therapeutic Deep Brain Stimulation in Parkinsonian Rats Directly Influences Motor Cortex. *Neuron* 76, 1030-1041. doi:10.1016/j.neuron.2012.09.032.

Li, S., Arbuthnott, G. W., Jutras, M. J., Goldberg, J. A., and Jaeger, D. (2007). Resonant Antidromic Cortical Circuit Activation as a Consequence of High-Frequency Subthalamic Deep-Brain Stimulation. *J Neurophysiol* 98, 3525-3537. doi:10.1152/jn.00808.2007.

Litvak, V., Eusebio, A., Jha, A., Oostenveld, R., Barnes, G., Foltynie, T., et al. (2012). Movement-related changes in local and long-range synchronization in parkinson's disease revealed by simultaneous magnetoencephalography and intracranial recordings. *J Neurosci* 32, 10541-10553. doi:10.1523/JNEUROSCI.0767-12.2012.

Lopez-Azcarate, J., Tainta, M., Rodriguez-Oroz, M. C., Valencia, M., Gonzalez, R., Guridi, J., et al. (2010). Coupling between beta and high-frequency activity in the human subthalamic nucleus may be a pathophysiological mechanism in Parkinson's disease. *J Neurosci* 30, 6667-6677. doi:10.1523/JNEUROSCI.5459-09.2010.

Mastro, K. J., and Gittis, A. H. (2015). Striking the right balance: Cortical modulation of the subthalamic nucleus-globus pallidus circuit. *Neuron* 85, 233-235. doi:10.1016/j.neuron.2014.12.062.

McConnell, G. C., So, R. Q., Hilliard, J. D., Lopomo, P., and Grill, W. M. (2012). Effective Deep Brain Stimulation Suppresses Low-Frequency Network Oscillations in the Basal Ganglia by Regularizing Neural Firing Patterns. *J Neurosci* 32, 15657-15668. doi:10.1523/JNEUROSCI.2824-12.2012.

McIntyre, C. C., and Hahn, P. J. (2010). Network perspectives on the mechanisms of deep brain stimulation. *Neurobiol Dis* 38, 329-337. doi:10.1016/j.nbd.2009.09.022.

Meissner, W., Leblois, A., Hansel, D., Bioulac, B., Gross, C. E., Benazzouz, A., et al. (2005). Subthalamic high frequency stimulation resets subthalamic firing and reduces abnormal oscillations. *Brain* 128, 2372-2382. doi:10.1093/brain/awh616.

Miocinovic, S., de Hemptinne, C., Chen, W., Isbaine, F., Willie, J. T., Ostrem, J. L., et al. (2018). Cortical Potentials Evoked by Subthalamic Stimulation Demonstrate a Short Latency Hyperdirect Pathway in Humans. *J Neurosci* 38, 9129-9141. doi:10.1523/JNEUROSCI.1327-18.2018.

Miocinovic, S., Somayajula, S., Chitnis, S., and Vitek, J. L. (2013). History, Applications, and Mechanisms of Deep Brain Stimulation. *JAMA Neurol* 70, 163. doi:10.1001/2013.jamaneurol.45.

Montgomery, Jr, E. B., and Gale, J. T. (2007). "Neurophysiology and Neurocircuitry," in *Handbook of Parkinson's Disease* Neurological Disease and Therapy., eds. R. Pahwa and K. E. Lyons (New York and London: CRC Press), 223-238. Available at: https://books.google.com/books?id=5ObndbjDuRcC.

Montgomery, E. (2004). Dynamically Coupled, High-Frequency Reentrant, Nonlinear Oscillators Embedded in Scale-Free Basal Ganglia-Thalamic-Cortical Networks Mediating Function and Deep Brain Stimulation Effects. *Nonlinear Stud* 11.

Montgomery, E. B. (2013). "Deep Brain Stimulation: Mechanisms of Action," in *Neurostimulation* (Oxford, UK: John Wiley & Sons, Ltd), 1-19. doi:10.1002/9781118346396.ch1.

Montgomery, E. B., and Gale, J. T. (2008). Mechanisms of action of deep brain stimulation (DBS). *Neurosci Biobehav Rev* 32, 388-407. doi:10.1016/j.neubiorev.2007.06.003.

Montgomery, E. B., Gale, J. T., and Huang, H. (2005). Methods for isolating extracellular action potentials and removing stimulus artifacts from microelectrode recordings of neurons requiring minimal operator intervention. *J Neurosci Methods* 144, 107-125. doi:10.1016/j.jneumeth.2004.10.017.

Moran, A., Stein, E., Tischler, H., Belelovsky, K., and Bar-Gad, I. (2011). Dynamic Stereotypic Responses of Basal Ganglia Neurons to Subthalamic Nucleus High-Frequency Stimulation in the Parkinsonian Primate. *Front Syst Neurosci* 5, 1-11. doi:10.3389/fnsys.2011.00021.

Moro, E., Esselink, R. J. A., Xie, J., Hommel, M., Benabid, A. L., and Pollak, P. (2002). The impact on Parkinson's disease of electrical parameter settings in STN stimulation. *Neurology* 59, 706-713. doi:10.1212/WNL.59.5.706.

Orfanidis, S. J. (1995). *Introduction to signal processing.* Prentice-Hall, Inc.

Oswal, A., Brown, P., and Litvak, V. (2013). Synchronized neural oscillations and the pathophysiology of Parkinson's disease. *Curr Opin Neurol* 26, 662-670. doi:10.1097/WCO.0000000000000034.

Özkurt, T. E., Butz, M., Homburger, M., Elben, S., Vesper, J., Wojtecki, L., et al. (2011). High frequency oscillations in the subthalamic nucleus: A neurophysiological marker of the motor state in Parkinson's disease. *Exp Neurol* 229, 324-331. doi:10.1016/j.expneurol.2011.02.015.

Ozturk, M., Abosch, A., Francis, D., Wu, J., Jimenez-Shahed, J., and Ince, N. F. (2019). Distinct subthalamic coupling in the ON state describes motor performance in Parkinson's disease. *Mov Disord.* doi:10.1002/mds.27800.

Ozturk, M., Kaku, H., Jimenez-Shahed, J., Viswanathan, A., Sheth, S. A., Kumar, S., et al. (2020a). Subthalamic Single Cell and Oscillatory Neural Dynamics of a Dyskinetic Medicated Patient With Parkinson's Disease. *Front Neurosci* 14, 1-8. doi:10.3389/fnins.2020.00391.

Ozturk, M., Telkes, I., Viswanathan, A., Jimenez-shahed, J., Tarakad, A., Kumar, S., et al. (2020b). Randomized, double-blind assessment of LFP versus SUA guidance in STN-DBS lead implantation: A Pilot Study. *Front Neurosci* [Accepted]. doi:10.3389/fnins.2020.00611.

Parker, J. L., Obradovic, M., Hesam Shariati, N., Gorman, R. B., Karantonis, D. M., Single, P. S., et al. (2020). Evoked Compound Action Potentials Reveal Spinal Cord Dorsal Column Neuroanatomy. *Neuromodulation Technol Neural Interface* 23, 82-95. doi:10.1111/ner.12968.

Priori, A., Foffani, G., Pesenti, A., Tamma, F., Bianchi, A. M., Pellegrini, M., et al. (2004). Rhythm-specific pharmacological modulation of subthalamic activity in Parkinson's disease. *Exp Neurol* 189, 369-379. doi:10.1016/j.expneurol.2004.06.001.

Reese, R., Leblois, A., Steigerwald, F., Potter-Nerger, M., Herzog, J., Mehdorn, H. M., et al. (2011). Subthalamic deep brain stimulation increases pallidal firing rate and regularity. *Exp Neurol* 229, 517-521. doi:10.1016/j.expneurol.2011.01.020.

Rizzone, M., Lanotte, M., Bergamasco, B., Tavella, A., Torre, E., Faccani, G., et al. (2001). Deep brain stimulation of the subthalamic nucleus in Parkinson's disease: effects of variation in stimulation parameters. *J Neurol Neurosurg Psychiatry* 71, 215-9. doi:10.1136/jnnp.71.2.215.

Rubin, J. E., and Terman, D. (2004). High Frequency Stimulation of the Subthalamic Nucleus Eliminates Pathological Thalamic Rhythmicity in a Computational Model. *J Comput Neurosci* 16, 211-235. doi:10.1023/BJCNS.0000025686.47117.67.

Saenger, V. M., Kahan, J., Foltynie, T., Friston, K., Aziz, T. Z., Green, A. L., et al. (2017). Uncovering the underlying mechanisms and whole-brain dynamics of deep brain stimulation for Parkinson's disease. *Sci Rep* 7, 9882. doi:10.1038/s41598-017-10003-y.

Santaniello, S., McCarthy, M. M., Montgomery, E. B., Gale, J. T., Kopell, N., and Sarma, S. V. (2015). Therapeutic mechanisms of high-frequency stimulation in Parkinson's disease and neural restoration via loop-based reinforcement. *Proc Natl Acad Sci* 112, E586-E595. doi:10.1073/pnas.1406549111.

Sharott, A., Gulberti, A., Zittel, S., Tudor Jones, A. A., Fickel, U., Munchau, A., et al. (2014). Activity Parameters of Subthalamic Nucleus Neurons Selectively Predict Motor Symptom Severity in Parkinson's Disease. *J Neurosci* 34, 6273-6285. doi:10.1523/jneurosci.1803-13.2014.

Sinclair, N. C., McDermott, H. J., Bulluss, K. J., Fallon, J. B., Perera, T., Xu, S. S., et al. (2018). Subthalamic nucleus deep brain stimulation evokes resonant neural activity. *Ann Neurol* 83, 1027-1031. doi:10.1002/ana.25234.

Sinclair, N. C., McDermott, H. J., Fallon, J. B., Perera, T., Brown, P., Bulluss, K. J., et al. (2019). Deep brain stimulation for Parkinson's disease modulates high-frequency evoked and spontaneous neural activity. *Neurobiol Dis* 130, 104522. doi:10.1016/j.nbd.2019.104522.

Soares, J., Kliem, M. A., Betarbet, R., Greenamyre, J. T., Yamamoto, B., and Wichmann, T. (2004). Role of External Pallidal Segment in Primate Parkinsonism: Comparison of the Effects of 1-Methyl-4-Phenyl-1,2,3,6-Tetrahydropyridine-Induced Parkinsonism and Lesions of the External Pallidal Segment. *J Neurosci* 24, 6417-6426. doi:10.1523/jneurosci.0836-04.2004.

Stefani, A., Fedele, E., Vitek, J., Pierantozzi, M., Galati, S., Marzetti, S., et al. (2011). The clinical efficacy of L-DOPA and STN-DBS share a common marker: Reduced GABA content in the motor thalamus. *Cell Death Dis* 2, 1-9. doi:10.1038/cddis.2011.35.

Stypulkowski, P. H., Giftakis, J. E., and Billstrom, T. M. (2011). Development of a Large Animal Model for Investigation of Deep Brain Stimulation for Epilepsy. *Stereotact Funct Neurosurg* 89, 111-122. doi:10.1159/000323343.

Swann, N. C., de Hemptinne, C., Miocinovic, S., Qasim, S., Wang, S. S., Ziman, N., et al. (2016). Gamma Oscillations in the Hyperkinetic State Detected with Chronic Human Brain Recordings in Parkinson's Disease. *J Neurosci* 36, 6445-6458. doi:10.1523/JNEUROSCI.1128-16.2016.

Telkes, I., Jimenez-Shahed, J., Viswanathan, A., Abosch, A., and Ince, N. F. (2016). Prediction of STN-DBS electrode implantation track in Parkinson's disease by using local field potentials. *Front Neurosci* 10, 1-16. doi:10.3389/fnins.2016.00198.

Thompson, J. A., Tekriwal, A., Felsen, G., Ozturk, M., Telkes, I., Wu, J., et al. (2018). Sleep patterns in Parkinson's disease: direct recordings from the subthalamic nucleus. *J Neurol Neurosurg Psychiatry* 89, 95-104. doi:10.1136/jnnp-2017-316115.

Urrestarazu, E., Iriarte, J., Alegre, M., Clavero, P., Rodriguez-Oroz, M. C., Guridi, J., et al. (2009). Beta activity in the subthalamic nucleus during sleep in patients with Parkinson's disease. *Mov Disord* 24, 254-260. doi:10.1002/mds.22351.

van Wijk, B. C. M., Beudel, M., Jha, A., Oswal, A., Foltynie, T., Hariz, M. I., et al. (2016). Subthalamic nucleus phase-amplitude coupling correlates with motor impairment in Parkinson's disease. *Clin Neurophysiol* 127, 2010-2019. doi:10.1016/j.clinph.2016.01.015.

Weinberger, M., Mahant, N., Hutchison, W. D., Lozano, A. M., Moro, E., Hodaie, M., et al. (2006). Beta Oscillatory Activity in the Subthalamic Nucleus and Its Relation to Dopaminergic Response in Parkinson's Disease. *J Neurophysiol* 96, 3248-3256. doi:10.1152/jn.00697.2006.

Welter, M.-L., Houeto, J.-L., Bonnet, A.-M., Bejjani, P.-B., Mesnage, V., Dormont, D., et al. (2004). Effects of High-Frequency Stimulation on Subthalamic Neuronal Activity in Parkinsonian Patients. *Arch Neurol* 61, 89. doi:10.1001/archneur.61.1.89.

Wichmann, T., and DeLong, M. R. (2006). "Basal ganglia discharge abnormalities in Parkinson's disease," in *Parkinson's Disease and Related Disorders* (Vienna: Springer Vienna), 21-25. doi:10.1007/978-3-211-45295-0_5.

Xu, W., Russo, G. S., Hashimoto, T., Zhang, J., and Vitek, J. L. (2008). Subthalamic Nucleus Stimulation Modulates Thalamic Neuronal Activity. *J Neurosci* 28, 11916-11924. doi:10.1523/JNEUROSCI.2027-08.2008.

Youngerman, B. E., Chan, A. K., Mikell, C. B., McKhann, G. M., and Sheth, S. A. (2016). A decade of emerging indications: deep brain stimulation in the United States. *J Neurosurg* 125, 461-471. doi:10.3171/2015.7.JNS142599.

Zhou, A., Johnson, B. C., and Muller, R. (2018). Toward true closed-loop neuromodulation: artifact-free recording during stimulation. *Curr Opin Neurobiol* 50, 119-127. doi: 10.1016/j.conb.2018.01.012.

Zhuang, Q. X., Li, G. Y., Li, B., Zhang, C. Z., Zhang, X. Y., Xi, K., et al. (2018). Regularizing firing patterns of rat subthalamic neurons ameliorates parkinsonian motor deficits. *J Clin Invest* 128, 5413-5427. doi:10.1172/JCI99986.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A method of determining brain stimulation parameters, the method comprising:
    applying Low Frequency Stimulation (LFS) to a subset of contacts of a multi-contact electrode implanted in a target structure in an individual's brain;
    measuring Evoked Compound Activity (ECA) evoked in the target structure by the LFS;
    extracting a phase space from the ECA;
    determining a range of frequencies for delivering brain stimulation within a predetermined range based on the phase space extracted from the ECA;
    applying High Frequency Stimulation (HFS) to the subset of contacts of the multi-contact electrode within the determined range of frequencies;
    measuring High Frequency Oscillations (HFO) evoked in the target structure by the applied HFS within the determined range;
    determining a frequency evoking HFO above a predetermined threshold;
    determining a corresponding power of a frequency of the HFO that is within the stimulation frequency range; and
    selecting the frequency as a treatment frequency for the target structure within the stimulation frequency range, wherein the frequency selected is associated with a maximum power of the powers corresponding to each HFO frequency evoked.

2. The method of claim 1, wherein the LFS is less than 100 Hz.

3. The method of claim 1, wherein the selected frequency is greater than 100 Hz.

4. The method of claim 1, wherein the selected frequency is about 130 Hz, about 160 Hz, or about 180 Hz.

5. The method of claim 1, wherein the measured HFO evoked in the target structure is from 200 Hz to 450 Hz.

6. The method of claim 1, wherein the ECA includes a resonating response above a predetermined threshold.

7. The method of claim 1, wherein if the ECA is below a predetermined threshold, the method further comprises applying a second LFS to a second subset of contacts of the multi-contact electrode in a different location within the target structure than the subset of contacts of the multi-contact electrode.

8. The method of claim 1, wherein the multi-contact electrode is configured for Deep Brain Stimulation (DBS) of the target structure.

9. The method of claim 1, wherein the target structure is the Subthalamic nucleus (STN).

10. The method of claim 1, wherein the individual has Parkinson's Disease (PD).

11. A system for determining deep brain stimulation parameters, comprising:
    at least one multi-contact electrode configured for implanting in a target structure in an individuals' brain;
    a stimulating device in electrical communication with the at least one multi-contact electrode, the stimulating device configured to apply Low Frequency Stimulation (LFS) or High Frequency Stimulation (HFS) to the at least one multi-contact electrode;
    a recording device configured to record at least one of Evoked Compound Activity (ECA) evoked in the target structure by the LFS and High Frequency Oscillations (HFO) evoked in the target structure by the HFS;
    a processor; and
    a memory, storing instructions thereon, which when executed by the processor, cause the system to:
        extract a phase space from the ECA;
        determine a range of frequencies for delivering brain stimulation within a predetermined range based on the phase space extracted from the ECA;
        analyze High Frequency Oscillations (HFO) evoked in the target structure by the applied HFS within the determined range;
        determine a frequency evoking HFO above a predetermined threshold;
        determine a corresponding power of a frequency of the HFO that is within the stimulation frequency range; and
        select the frequency as a treatment frequency for the target structure within the stimulation frequency range, wherein the frequency selected is associated with a maximum power of the powers corresponding to each HFO frequency evoked.

12. The system of claim 11, wherein the stimulating device is configured to selectively apply the LFS or HFS to a subset of contacts of one multi-contact electrode of the plurality of multi-contact electrodes.

13. The system of claim 11, wherein at least one of the stimulating device, the recording device, or the processor is implanted in the individual's chest.

14. The system of claim 13, further including an input/output (I/O) unit in electrical communication with the stimulating device, the recording device, and the processor.

15. The system of claim 11, wherein the LFS is less than 50 Hz.

16. The system of claim 11, wherein the selected frequency is greater than 130 Hz.

17. The system of claim 11, wherein the selected frequency is about 130 Hz, about 160 Hz, or about 180 Hz.

18. The system of claim 11, wherein the HFO evoked in the target structure is from 200 Hz to 450 Hz.

19. The system of claim 11, wherein the multi-contact electrode is configured for Deep Brain Stimulation (DBS) of the target structure.

20. The system of claim 11, wherein the target structure is the Subthalamic nucleus (STN).

* * * * *